US00PP30786P3

(12) United States Plant Patent
Randag

(10) Patent No.: US PP30,786 P3
(45) Date of Patent: Aug. 6, 2019

(54) CALLA LILY PLANT NAMED 'QATAR'

(50) Latin Name: *Zantedeschia sprengeri*
Varietal Denomination: Qatar

(71) Applicant: Sunglory Beheer B.V., Schagerbrug (NL)

(72) Inventor: Cecilius Jan-Jochem Randag, 't Zand (NL)

(73) Assignee: Sunglory Beheer B.V., Schagerbrug (NL)

( * ) Notice: Subject to any disclaimer, the term of this patent is extended or adjusted under 35 U.S.C. 154(b) by 0 days.

(21) Appl. No.: 15/732,673

(22) Filed: Dec. 13, 2017

(65) Prior Publication Data

US 2018/0184567 P1 Jun. 28, 2018

Related U.S. Application Data

(60) Provisional application No. 62/498,157, filed on Dec. 15, 2016.

(51) Int. Cl.
*A01H 6/10* (2018.01)
*A01H 5/02* (2018.01)

(52) U.S. Cl.
USPC ..... Plt./490
CPC ..... *A01H 5/02* (2013.01)

(58) Field of Classification Search
USPC ..... Plt./490
CPC ..... A01H 6/10; A01H 5/02
See application file for complete search history.

*Primary Examiner* — Keith O. Robinson
(74) *Attorney, Agent, or Firm* — The Webb Law Firm

(57) ABSTRACT

'Qatar' is a new variety of calla lily plant having inflorescences with a yellow/orange-colored spathe that produces 5-34 inflorescences per tuber. The height of the top of an inflorescence above the soil can reach up to 45 cm. The leaves are green with transparent maculations present and have a leathery texture.

2 Drawing Sheets

Botanical classification: *Zantedeschia sprengeri*.
Varietal denomination: 'Qatar'.

BACKGROUND OF THE NEW PLANT

The present invention comprises a new and distinct cultivar of calla lily, botanically known as *Zantedeschia sprengeri* and hereinafter referred to by the cultivar name 'Qatar'.

'Qatar' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z981035 (female parent, unpatented) with a *Zantedeschia sprengeri* selection referred to as Z010367 (male parent, unpatented). 'Qatar' was selected in 2008 by the inventor in 't Zand, The Netherlands as one flowering plant within the progeny of the stated cross.

The first act of asexual reproduction of 'Qatar' by tissue culture was performed by the inventor in September of 2010 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S.

Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Qatar' which, in combination, distinguish this calla lily as a new and distinct cultivar:

1. Yellow/orange-colored spathes;
2. High inflorescence production; and
3. Fast forcing time.

Further, when compared to calla lily plant named 'Mercedes' (unpatented), the upper surface spathe color of 'Mercedes' varies between Red Group RHS 46C and 46D, whereas the upper surface spathe color of 'Qatar' is Yellow Group RHS 13A, with a secondary color that varies between Orange-Red Group RHS 32B and 34B.

Table 1 provides similarities and differences of 'Qatar' to its parents, *Zantedeschia sprengeri* selection Z981035 and *Zantedeschia sprengeri* selection Z010367.

TABLE 1

| 'Qatar' | Similarities | Differences |
|---|---|---|
| Z981035 | Spathe size<br>Number of inflorescences<br>Forcing time | Spathe color<br>Spathe shape |
| Z010367 | Spathe color<br>Leaf maculations | Spathe shape<br>'Qatar' has a smaller spathe size |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
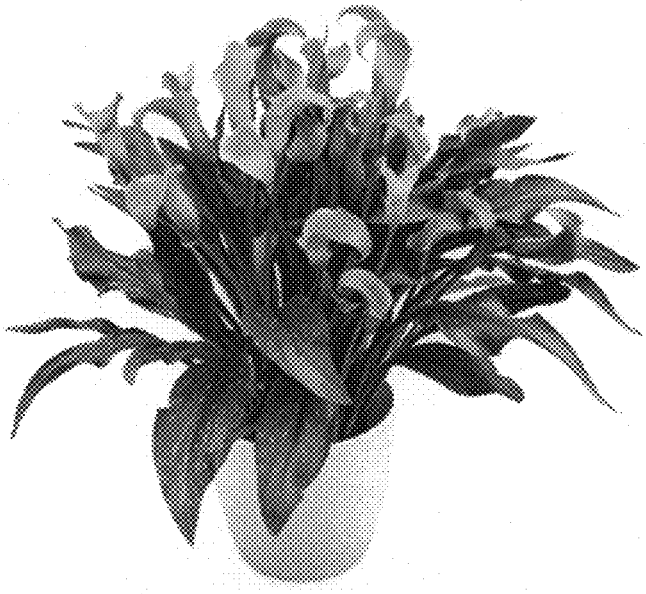
FIG. 1 is a photograph of a potted plant of the new variety.
Figure 2:
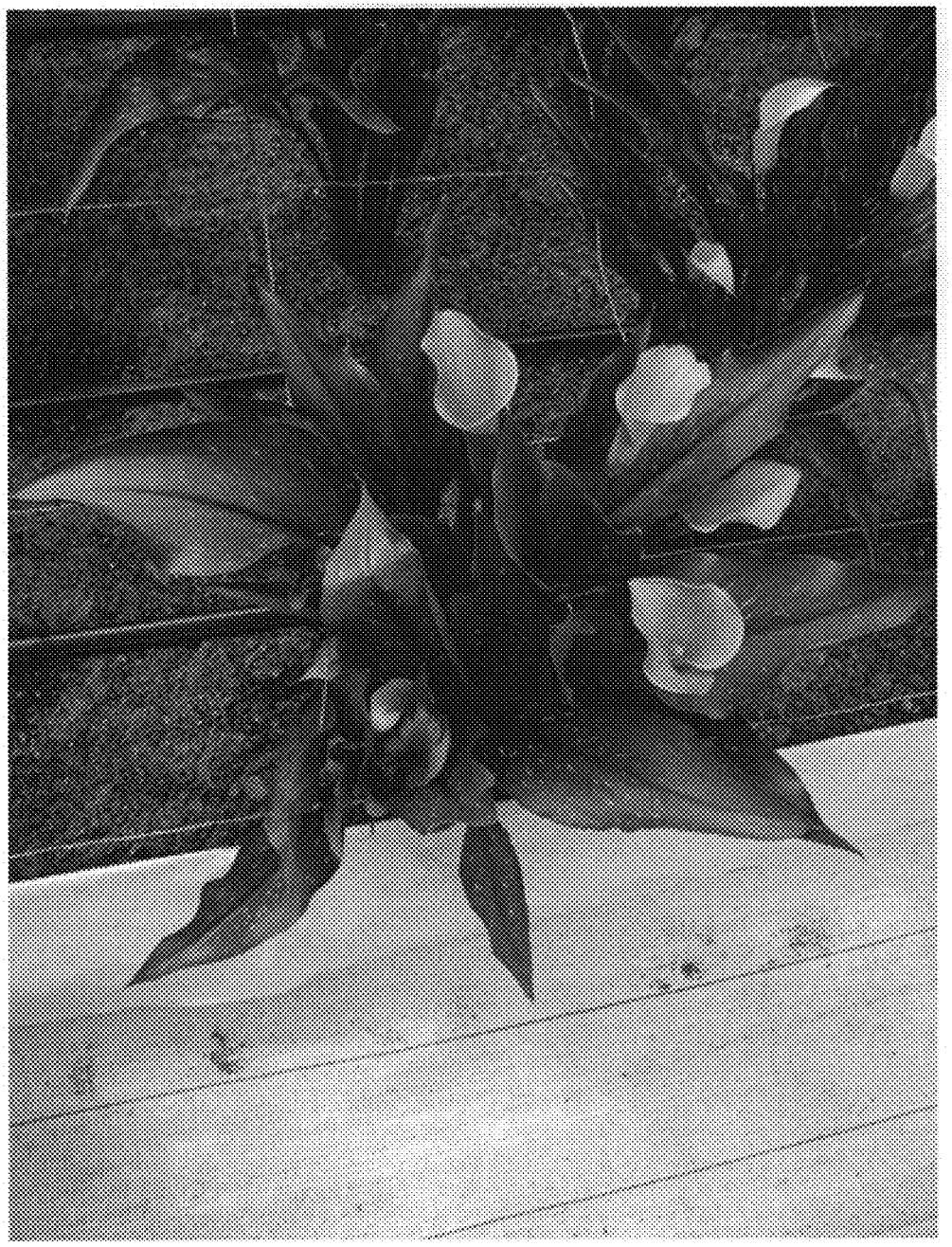
FIG. 2 is a photograph of a top view of a plant of the new variety.

Type: Deciduous.

Size:

*Height of the leaf canopy above the soil.*—19-45 cm.

*Height of top of inflorescences above the soil.*—20-45 cm.

*Diameter.*—10-14 cm.

Form: Erect.

Number of inflorescences per tuber:

*Size* 14-16 *cm in diameter.*—5-9 inflorescences.

*Size* 16-18 *cm in diameter.*—10-17 inflorescences.

*Size* 18-20 *cm in diameter.*—12-20 inflorescences.

*Size* 20+ *cm in diameter.*—17-34 inflorescences.

Branches:

*Average number.*—8.5.

*Color.*—Between Green Group RHS 143A and Yellow-Green Group RHS 144B.

Young shoot color: Between Green Group RHS 143A and Yellow-Green Group RHS 144B.

Leaves:

*Size.*—Width: 2.5-9 cm, with broadest part slightly below the middle. Length: 14-26 cm.

*Number per plant.*—31-53.

*Leaf blade lobes.*—None present.

*Shape.*—Lanceolate.

*Apex.*—Acuminate.

*Base.*—Decurrent.

*Margin.*—Undulate; having a color between Yellow-Green Group RHS 144A and 144B.

*Color.*—Upper surface: Green Group RHS 137B to Yellow-Green Group RHS 146C, having transparent maculations of approximately White Group RHS 155A. Lower surface: Yellow-Green Group RHS 146A to 146B, having transparent maculations of approximately White Group RHS 155A.

*Veins.*—Configuration: Pinnate. Color: Upper Surface: Yellow-Green Group RHS 144A. Lower Surface: Green Group RHS 143A to Yellow-Green Group RHS 144A.

*Surface texture.*—Smooth (both surfaces).

*Petiole.*—Length: 7-20 cm. Diameter: 3-9 mm Color: The base is White Group RHS 155A, the upper part is Green Group RHS 143A to Yellow-Green Group RHS 144B.

Roots:

*Color.*—Between White Group RHS 155C and 155D.

*Branching description.*—Fibrous root system. Several main roots emerge from the top of the tuber and form a small number of lateral roots.

The Inflorescence and Seeds

Spathe:

*Size.*—Length (measured from opening to tip): 5-7 cm. Width: 2.5-4 cm. Height: 5-9 cm.

*Color.*—Throat spot: Absent. Upper surface: Yellow Group RHS 13A, with a secondary color that varies between Orange-Red Group RHS 32B and 34B. Lower surface: Varies between Yellow Group RHS 13A and 13B, with a secondary color that varies between Orange-Red Group RHS 32B and 33B.

*Vein color.*—Between Yellow Group RHS 13A and 13B.

*Shape.*—Funnel.

*Apex.*—Acuminate.

*Base.*—Attenuate.

*Margin.*—Undulate.

*Texture.*—Smooth (upper and lower surfaces).

Spadix:

*Size.*—Length: 25-36 mm. Diameter: 5-9 mm.

*Color.*—Between Yellow Group RHS 13A and Yellow-Orange Group RHS 14B.

*Position relative to spathe.*—Upright.

Peduncle:

*Size.*—Length: 15-36 cm. Diameter: 4-9 mm.

*Color.*—The upper part is between Yellow-Green Group RHS 144A and 144B, the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 600 and 840. Pollen amount: Abundant; similar to 'Picasso' (U.S. Plant Pat. No. 15,282). Color: Between White Group RHS 155A and 155B.

*Anther.*—Shape: Round. Length: Less than 1 mm. Color: Between Yellow Group RHS 13A and Yellow-Orange Group RHS 14B.

*Filament.*—Length: Less than 1 mm. Color: Between White Group RHS 155A and 155B.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 13A and Yellow-Orange Group RHS 14B.

*Ovaries.*—Texture: Smooth. Length: Between 1 to 10 mm. Width: Between 1 to 10 mm. Color: Top color is between Yellow-Green Group RHS 145C and 145D, the bottom color is between White Group RHS 155B to Green-White Group RHS 157C.

Seeds:

*Length.*—4-7 mm.

*Width.*—3-6 mm.

*Color*.—Between Yellow-Green Group RHS 150A and 151A.

*Amount*.—Between 1-60.

General

Disease resistance: No unusual susceptibility/resistance to diseases noticed to date.

Pest resistance: No unusual susceptibility/resistance to pests noticed to date.

Heat tolerance: No heat tolerance.

Hardiness: Not hardy.

Flowering: In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Qatar' as herein described and illustrated.

* * * * *